(12) United States Patent
Smith et al.

(10) Patent No.: US 10,456,789 B2
(45) Date of Patent: Oct. 29, 2019

(54) PIPETTE WASH

(71) Applicant: Douglas Scientific, LLC, Alexandria, MN (US)

(72) Inventors: Chad Steven Smith, Battle Lake, MN (US); Jacob Hendrickx, Campbell, MN (US); Hans A. Mische, Grey Eagle, MN (US)

(73) Assignee: DOUGLAS SCIENTIFIC, LLC, Alexandria, MN (US)

( * ) Notice: Subject to any disclaimer, the term of this patent is extended or adjusted under 35 U.S.C. 154(b) by 0 days.

(21) Appl. No.: 14/888,005

(22) PCT Filed: May 1, 2014

(86) PCT No.: PCT/US2014/036390
§ 371 (c)(1),
(2) Date: Oct. 29, 2015

(87) PCT Pub. No.: WO2014/179584
PCT Pub. Date: Nov. 6, 2014

(65) Prior Publication Data
US 2016/0101423 A1    Apr. 14, 2016

Related U.S. Application Data

(60) Provisional application No. 61/818,099, filed on May 1, 2013.

(51) Int. Cl.
*B08B 9/032* (2006.01)
*B01L 3/02* (2006.01)
(Continued)

(52) U.S. Cl.
CPC ............. *B01L 99/00* (2013.01); *B01L 3/0275* (2013.01); *B08B 9/0323* (2013.01); *G01N 35/1004* (2013.01); *B01L 2400/049* (2013.01)

(58) Field of Classification Search
CPC .... B08B 9/0323; G01N 35/1004; B01L 3/021
See application file for complete search history.

(56) References Cited

U.S. PATENT DOCUMENTS 4,029,487 A * 6/1977 Brandt ............... B01D 46/2407
137/202
6,475,444 B1   11/2002 Zimmermann et al.
(Continued)

FOREIGN PATENT DOCUMENTS

DE          10207499 A1 *  9/2003 ............... B08B 3/02
WO          WO9703766      2/1997

OTHER PUBLICATIONS

Machine translation: DE10207499; Ehlert et al., 2003.*
(Continued)

*Primary Examiner* — Mikhail Kornakov
*Assistant Examiner* — Natasha N Campbell
(74) *Attorney, Agent, or Firm* — Greenberg Traurig, LLP

(57) ABSTRACT

A method of washing an array of pipette tips (94) with residual biological material includes lowering the array of pipette tips (94) into a wash basin (20) that includes an array of flush ports (22). A vacuum is generated such that the residual biological material in the array of pipette tips (94) is evacuated through the array of flush ports (22). A wash cycle is performed that includes raising the array of pipette tips (94) from the wash basin (20), filling the wash basin (20) with a primary wash fluid, lowering the array of pipette tips (94) into the wash basin (20), miming a pipette tip cleansing cycle, and generating a vacuum such that the primary wash fluid in the array of pipette tips (94) and the wash basin (20) is evacuated through the array of flush ports (22).

21 Claims, 8 Drawing Sheets

(51) Int. Cl.
*G01N 35/10* (2006.01)
*B01L 99/00* (2010.01)

(56) References Cited

U.S. PATENT DOCUMENTS

| | | | |
|---|---|---|---|
| 6,632,653 | B1 | 10/2003 | Astle |
| 6,955,180 | B2 | 10/2005 | Kocherlakota et al. |
| 7,153,689 | B2 | 12/2006 | Tolosko et al. |
| 8,449,839 | B2 | 5/2013 | Rajagopal et al. |
| 8,921,539 | B2 | 12/2014 | Suh et al. |
| 2002/0009391 | A1 | 1/2002 | Marquiss et al. |
| 2003/0026732 | A1 | 2/2003 | Gordon et al. |
| 2004/0047765 | A1 | 3/2004 | Gordon et al. |
| 2005/0170512 | A1 | 8/2005 | Rubin et al. |
| 2006/0081539 | A1* | 4/2006 | Safar .................. B01L 3/5082 210/695 |
| 2006/0266130 | A1* | 11/2006 | Zobel .................. B03C 1/286 73/864.02 |
| 2007/0123999 | A1 | 5/2007 | Raghibizadeh et al. |
| 2009/0186374 | A1 | 7/2009 | Okun et al. |
| 2012/0211026 | A1 | 8/2012 | Schoeneck |
| 2014/0023569 | A1 | 1/2014 | Schoeppe et al. |
| 2014/0318574 | A1 | 10/2014 | Safavi |
| 2016/0016161 | A1* | 1/2016 | Schoeneck ......... G01N 35/1004 73/863.32 |

OTHER PUBLICATIONS

International Search Report and Written Opinion from PCT Application Serial No. PCT/US2014/036390, dated Sep. 8, 2014, 10 pages.

Caldwell, E. "A wash protocol to Determine and Eliminate Liquid Carry-Over Using the Thermo Scientific Matrix PlateMate 2×2 with Stainless Steel Syringes" Thermo Scientific Technocal Note: 07005. Publication [online]. 2008 [retrived on Jul. 30, 2014].

Mir, Mohammad Muzaffar et al. 'How to decontaminate pipettes?'. In ResearchGate [online]. Apr. 12, 2013 [retrieved on Jul. 31, 2014].

* cited by examiner

PIPETTE WASH

CROSS-REFERENCE TO RELATED APPLICATION(S)

This application claims priority from U.S. Provisional Application No. 61/818,099, filed May 1, 2013 for "PIPETTE WASH" by Chad Steven Smith et al.

BACKGROUND

The present invention relates to inline sample processing on Douglas Scientific's Nexar® platform, and more specifically relates to a pipette wash for a dispensing system.

Advances in the biosciences industry have created a demand for high throughput biological sample processing and detection systems. For example, Astle, U.S. Pat. No. 6,632,653, discloses a high throughput method of performing biological assays using a tape with a matrix of wells. In a high throughput system, the source and assay are transferred from microplates into the tape, the tape is sealed, and the tape is accumulated on spools. The tape containing samples, such as biological samples, is then transferred to a water bath product and a reaction may be performed, such as polymerase chain reaction (PCR) using thermocycling. Subsequently, the tape may be loaded onto a detection instrument, which detects presence of a desired analyte, such as nucleic acid presence in a biological sample.

Pipette tips for sample dispensing in such high throughput systems are commonly used once to transfer a biological sample into the tape wells due to the risk of cross contamination associated with reusing pipette tips. Consumable materials like pipette tips increase costs associated with high throughput systems due to the cost of the pipette tips and waste disposal. With a push towards increasing reaction speeds to process even more samples at an ever faster rate, pipette tip costs could become prohibitively expensive.

SUMMARY

A method of washing an array of pipette tips with residual biological material includes lowering the array of pipette tips into a wash basin that includes an array of flush ports. A vacuum is generated such that the residual biological material in the array of pipette tips is evacuated through the array of flush ports. A wash cycle is performed that includes raising the array of pipette tips from the wash basin, filling the wash basin with a primary wash fluid, lowering the array of pipette tips into the wash basin, running a pipette tip cleansing cycle, and generating a vacuum such that the primary wash fluid in the array of pipette tips and the wash basin is evacuated through the array of flush ports.

In another embodiment, a system for washing an array of pipette tips with residual biological material includes a wash basin with an array of flush ports for receiving the array of pipette tips, a primary pump for filling the wash basin with a primary wash fluid, and a vacuum generator for generating a vacuum such that the primary wash fluid and residual biological material in the array of pipette tips and the wash basin is evacuated through the array of flush ports.

DETAILED DESCRIPTION

The present disclosure includes a fully automated pipette wash that provides tip cleaning functionality to a dispensing system, allowing pipette tips to be reused with minimal cross contamination. A dispensing system is used to aspirate samples from sample plates and dispense samples into a tape with a matrix of wells. To ensure that the desired amount of biological sample is dispensed into the tape, the dispensing system aspirates more sample than necessary. When the sample is dispensed into the tape, residual sample material, including the volume overage, remains in the pipette tips of the dispensing system. When pipette tips are reused, the pipette wash reduces the potential for residual material from a previous dispensing cycle to be deposited into the tape in a later dispensing cycle.

Figure 1:
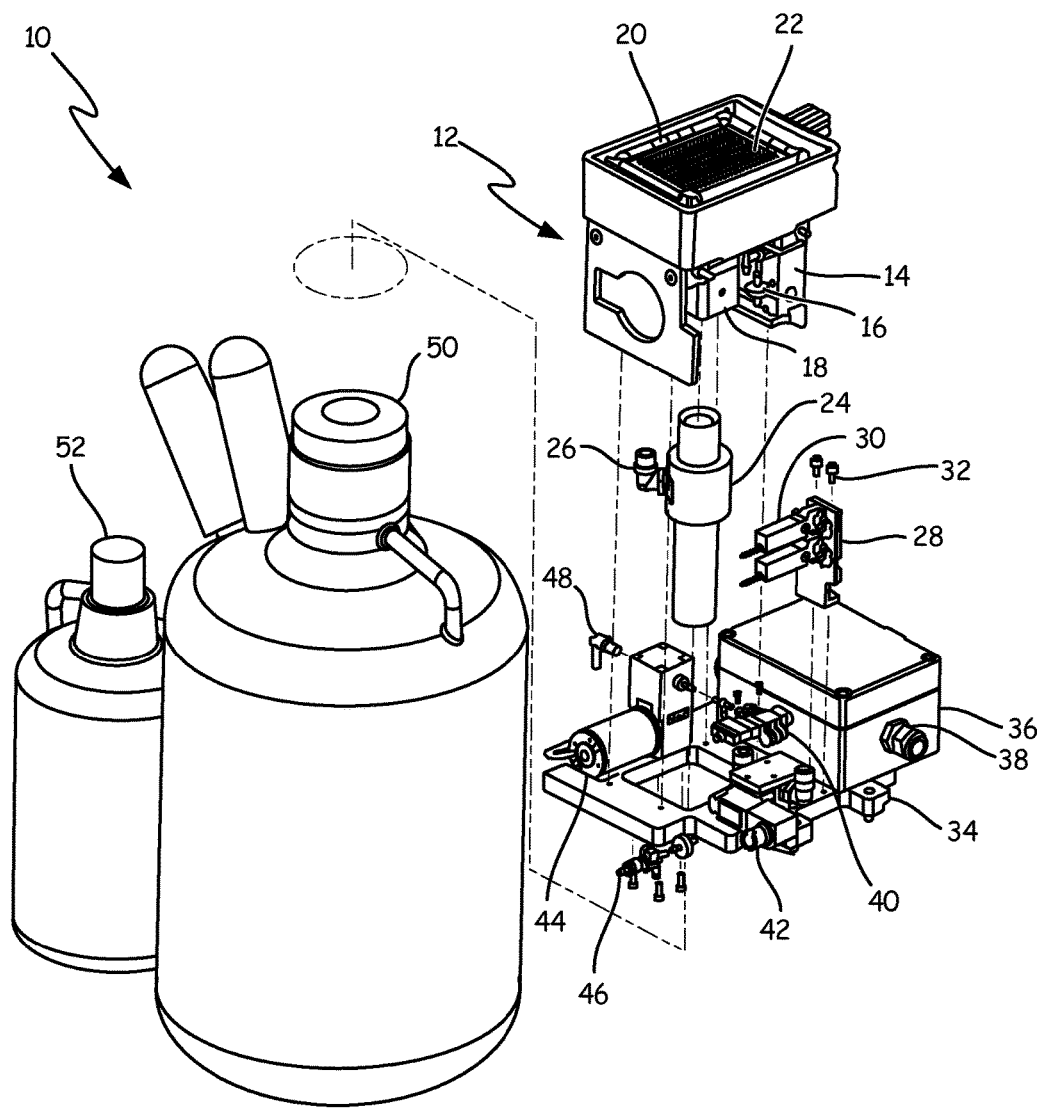
FIG. 1 is a partial perspective and partial exploded view of a pipette wash system.

FIG. 1 is a partial perspective and partial exploded view of pipette wash system 10. Pipette wash system 10 includes pipette wash sub assembly 12 with pump 14, wash fluid check valve 16, venturi adapter 18, and discrete tip wash basin 20 with flush array 22. Pipette wash system 10 further includes vacuum pump 24 with air line fitting 26, valve bracket 28 with valve 30 and fasteners 32, wash mounting plate 34, electrical enclosure 36 with cable/cord port 38, air cylinder valve/fitting assembly 40, vacuum pump valve 42, pump 44, wash fluid fittings 46 and 48, carboy 50, and jug 52.

Valve 30 is mounted to valve bracket 28, and fasteners 32 attach valve bracket 28 to mounting plate 34. Electrical enclosure 36 with cable/cord port 38 is mounted on mounting plate 34 and contains all of the electronics to control pipette wash system 10. Air cylinder valve/fitting assembly 40 is attached to electrical enclosure 36. Vacuum pump valve 42 is mounted to mounting plate 34 and turns vacuum pump 24 on and off. Vacuum pump 24 passes through an opening in mounting plate 34 and connects pipette wash sub assembly 12 to carboy 50. Air line fitting 26 connects an air line to vacuum pump 24. Pump 44 and pipette wash sub assembly 12 are also mounted on wash mounting plate 34. Wash fluid fittings 46 and 48 connect wash fluid lines to pump 44.

Pipette wash sub assembly 12 is the portion of pipette wash system 10 that comes into contact with pipette tips from a dispensing system in order to clean the pipette tips. Pipette wash sub assembly 12 includes discrete tip wash basin 20, which may be, for example, made of noryl or any other suitable material that is well suited for alkalines and acids. In an alternative embodiment, discrete tip wash basin 20 may be, for example, made of a clear material that allows ultraviolet light to travel through discrete tip wash basin 20 to treat pipette tips as they are lowered into discrete tip wash basin 20. Discrete tip wash basin 20 includes flush array 22, an array of ports for evacuating liquid and biological waste during operation of pipette wash system 10. Flush array 22 may include an array of 384 ports, for example. In an alternative embodiment, flush array 22 may include an array of 96 ports. Pump 44 pumps a wash fluid, such as a cleaning solution of bleach containing 6% sodium hypochlorite, for example, from jug 52, through wash fluid check valve 16, and into discrete tip wash basin 20 to flood discrete tip wash basin 20. Pump 44 pumps a wash fluid, such as water, for example, through wash fluid check valve 16 into discrete tip wash basin 20.

Discrete tip wash basin 20 is designed to work with vacuum pump 24 to create a discrete vacuum on each pipette tip of a dispensing system, subsequently maximize the suction effect around each pipette tip, and finally reduce or eliminate any remaining or residual wash fluid. Venturi adapter 18 receives vacuum pump 24, which is a material conveying pump that provides a large volume of air flow to pipette wash sub assembly 12 in order to provide a uniform vacuum for evacuating material from discrete tip wash basin 20 through flush array 22. Vacuum pump 24 is configured to provide a uniform vacuum such that there is a vacuum draw on every open port of flush array 22. If the pressure is right and the draw is thorough from vacuum pump 24, flush array 22 may be an array of any number of ports. In one embodiment, flush array 22 may include a single (one) port. In an alternative embodiment, flush array 22 may include 96 ports. In an alternative embodiment, flush array 22 may include 384 ports. Carboy 50 receives material evacuated from discrete tip wash basin 20 through flush array 22.

Figure 2:
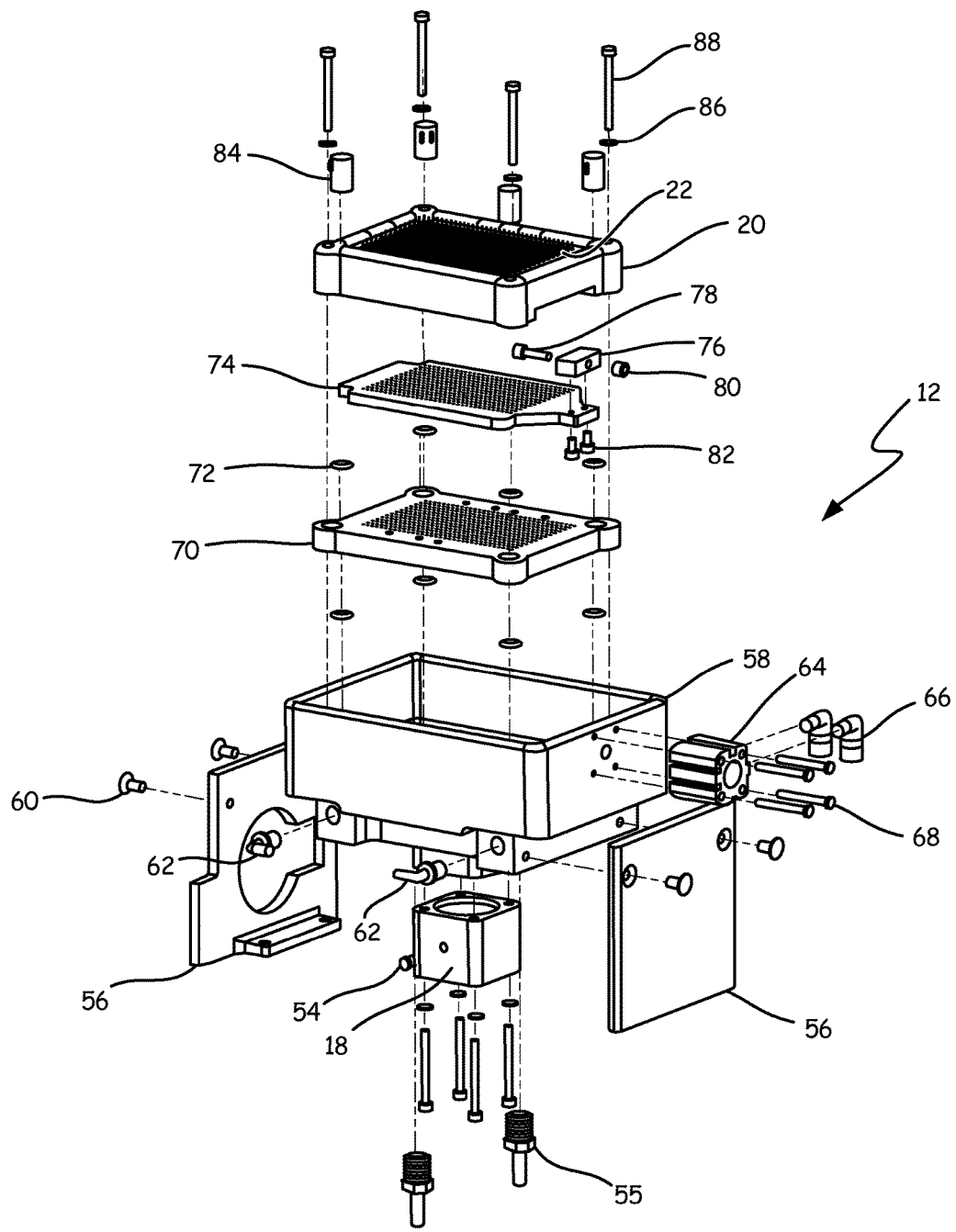
FIG. 2 is an exploded view of the pipette wash sub assembly of the pipette wash system of FIG. 1.

FIG. 2 is an exploded view of pipette wash sub assembly 12. Pipette wash sub assembly 12 includes venturi adapter 18, discrete tip wash basin 20 with flush array 22, screw set 54, drain hose fittings 55, wash stands 56, wash tub 58, fasteners 60, wash fluid hose fittings 62, air cylinder 64, air cylinder fittings 66, fasteners 68, wash base 70, washers 72, wash valve plate 74, mount block 76, fastener 78, mount spacer 80, fasteners 82, wash jets 84, washers 86, and fasteners 88.

Wash stands 56 are connected to wash tub 58 with fasteners 60. Wash tub 58 holds wash base 70, wash valve plate 74, and discrete tip wash basin 20. Wash fluid hose fittings connect wash fluid supplies to wash tub 58. Wash jets 84 port wash fluid into discrete tip wash basin 20. Discrete tip wash basin 20 stacks on top of wash valve plate 74, which stacks on top of wash base 70. Mount block 76, fastener 78, mount spacer 80, and fasteners 82 connect wash valve plate 74 to air cylinder 64. Fasteners 68 connect air cylinder 64 to wash tub 58. Air cylinder fittings 66 connect air cylinder to an air supply.

Wash valve plate 74 includes an array of valves that line up with the array of ports in flush array 22 of discrete tip wash basin 20. In one embodiment, wash valve plate 74 may include an array of 384 valves. In another embodiment, wash valve plate 74 may include an array of 96 valves. In another embodiment, wash valve plate 74 may include a single (one) valve. Wash valve plate 74 works with vacuum pump 24 in order to control vacuum timing. Air cylinder valve/fitting assembly 40 turns air cylinder 64 on to shift wash valve plate 74 in order to allow fluid evacuation from discrete tip wash basin 20. When wash valve plate 74 shifts, all wash fluids are evacuated from discrete tip wash basin 20 within seconds.

Figure 3:
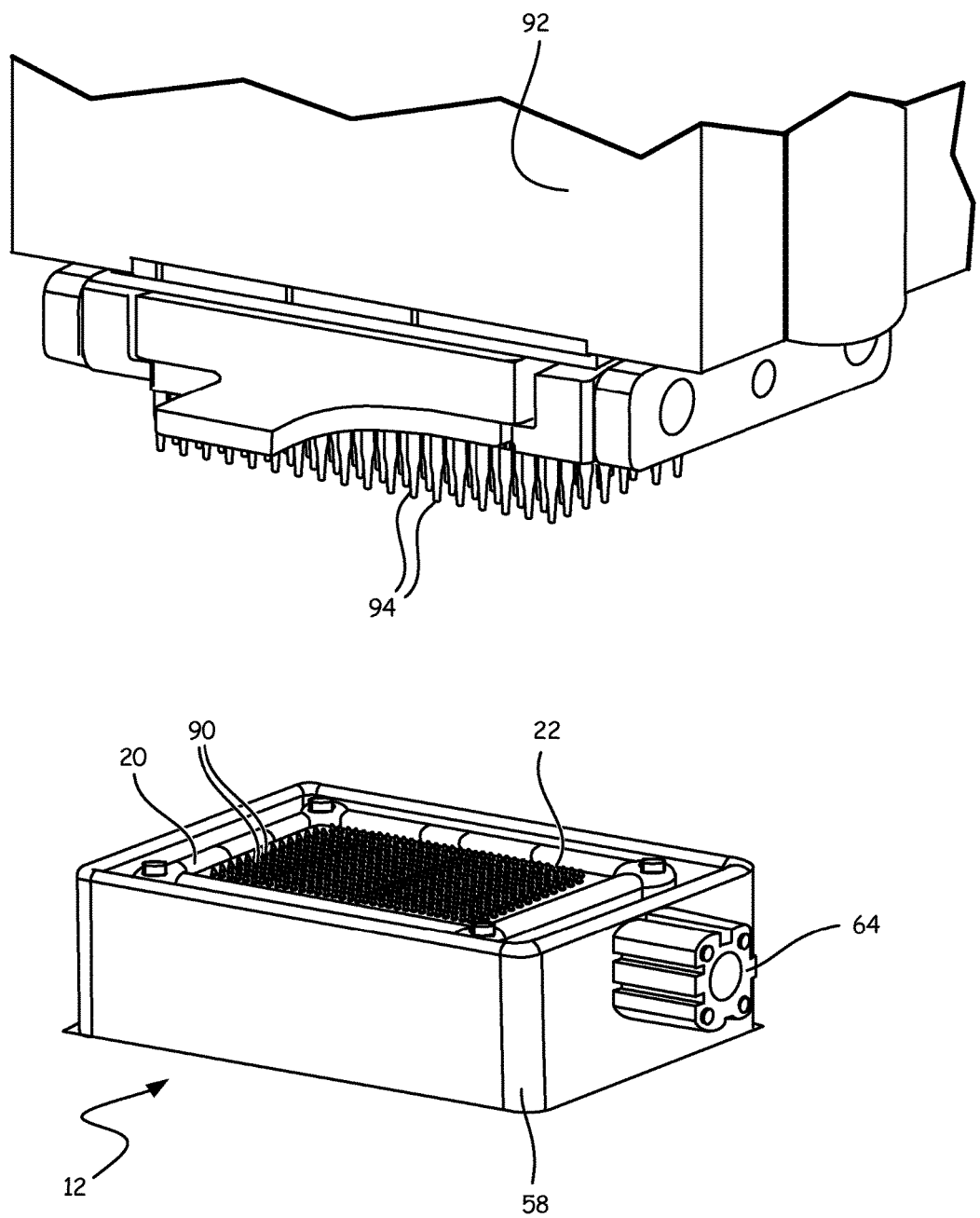
FIG. 3 is a perspective view of the pipette wash sub assembly of the pipette wash system of FIG. 1 and a dispensing jet system.

FIG. 3 is a perspective view of pipette wash sub assembly 12 and dispensing jet system 92. Pipette wash sub assembly 12 includes wash tub 58, air cylinder 64, wash jets 84, and discrete tip wash basin 20 with flush array 22 and fingers 90. Dispensing jet system 92 includes pipette tips 94. Pipette tips 94 may be arranged in an array of 384 tips. In an alternative embodiment, pipette tips 94 may be arranged in an array of 96 tips. In an alternative embodiment, pipette tips 94 may include a single (one) pipette tip. The ports of flush array 22 are aligned with pipette tips 94 in order to evacuate material from pipette tips 94. Fingers 90 of discrete tip wash basin 20 reduce surface area on which wash fluid can sit, allowing effective evacuation of wash fluid through flush array 22. Fingers 90 form an undulating surface to create a non-planar surface with minimal surface area at any one point. This facilitates fast and complete evacuation of a wash solution from wash basin 20 and reduces the amount of residual wash solution in wash basin 20.

Referring now to FIGS. 1-3, in a high throughput system dispensing jet system 92 aspirates a predetermined volume of biological material, such as genetic fluid from soy or corn, for example, into each of pipette tips 94 at the same time. The volume aspirated includes a volume overage in order to ensure dispensing accuracy. Upon completion of this aspiration step, dispensing jet system 92 shifts over to an array tape into which dispensing jet system 92 dispenses a predetermined amount of biological material. Dispensing jet system 92 then shifts over to pipette wash system 10 and lowers pipette tips 94 down into discrete tip wash basin 20, dispensing the remaining biological material while a flush cycle simultaneously begins. Dispensing jet system 92 may, for example, include a vibration system in order to assist in dislodging biological material from pipette tips 94.

In the flush cycle, vacuum pump 24 creates a vacuum such that the remaining biological material in pipette tips 94 is evacuated through flush array 22 and wash valve plate 74, and disposed of in carboy 50. Dispensing jet system 92 rises while pipette wash system 10 finishes the flush cycle. Pipette wash system 10 then begins a fill cycle by filling discrete tip wash basin 20 with a wash solution. In one embodiment, pump 44 pumps a primary fluid into discrete tip wash basin 20 to fill discrete tip wash basin 20. Depending on the biological material, a secondary fluid, such as bleach, may be needed to clean pipette tips 94. Therefore, in an alternative embodiment pump 14 pumps a secondary fluid, such as bleach, for example, into discrete tip wash basin 20 and adds a primary fluid, such as water to obtain a desired percentage of secondary fluid in discrete tip wash basin 20. During each fill cycle, discrete tip wash basin 20 is filled with approximately 90 mL of water.

As discrete tip wash basin 20 is filled with the wash solution, dispensing jet system 92 lowers pipette tips 94 back down and begins a series of dispensing pipette piston cycles, aspirating and dispensing the wash solution in pipette tips 94. In an alternative embodiment, pipette tips 94 may be detachable such that pipette tips 94 are released onto discrete tip wash basin 20 and a secondary head of dispensing system 92 flows wash fluid through pipette tips 94. The number of dispensing pipette piston cycles may range from 1 to 24 cycles, varying depending on application optimization.

Once the dispensing pipette piston cycles are complete, vacuum pump 24 creates a vacuum such that the wash solution is evacuated from discrete tip wash basin 20 and pipette tips 94 through flush array 22 and wash valve plate 74, and disposed of in carboy 50. Dispensing jet system 92 rises while pipette wash system 10 finishes the flush cycle. The fill and flush cycles make up one complete wash cycle. The wash cycle is repeated until pipette tips 94 are satisfactorily cleaned. The number of wash cycles is typically 3-4 cycles, but may vary from 1-6 cycles depending on application optimization. The entire wash process lasts just over one minute.

In an alternative embodiment, pipette wash system 10 may include, for example, an ultraviolet light apparatus in discrete tip wash basin 20 to aid in neutralizing biological material from pipette tips 94. The ultraviolet light apparatus could be a ring light, point light, or another other suitable light apparatus that would aid in neutralizing biological material from pipette tips 94. In another alternative embodiment, pipette wash system 10 and dispensing system 92 may include a shroud that surrounds the pipette head of pipette tips 94, pipette tips 94 and discrete tip wash basin 20. Ultraviolet light may be shone into the shroud in order to assist in neutralizing biological material from pipette tips 94.

Figure 4A:
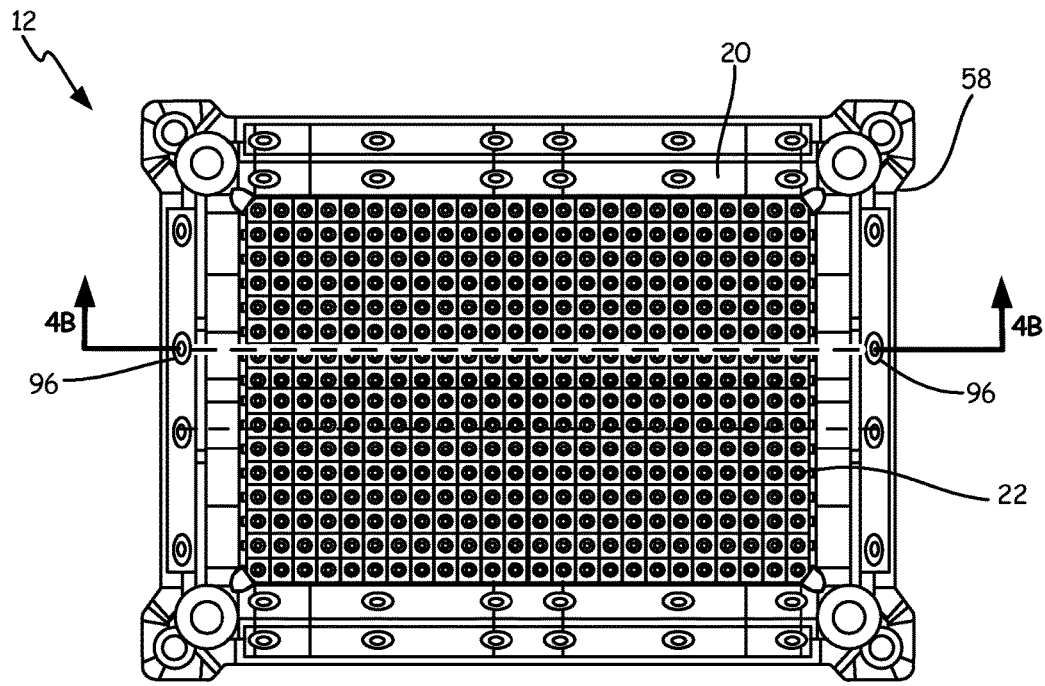
FIG. 4A is a top view of the pipette wash sub assembly of FIG. 3 with vacuum ports.
Figure 4B:
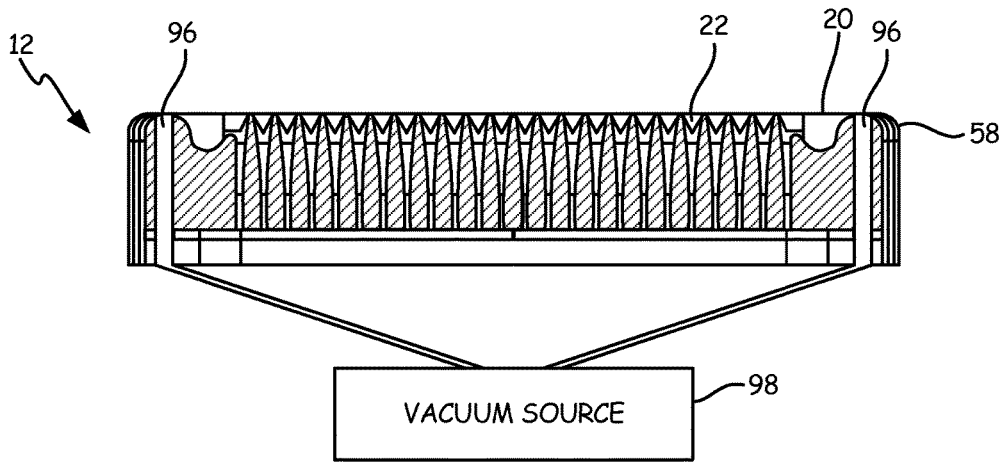
FIG. 4B is a cross-sectional view of the pipette wash subassembly of FIG. 4A along line 4B-4B.

FIG. 4A is a top view of pipette wash sub assembly 12. FIG. 4B is a cross-sectional view of pipette wash subassembly 12 along line 4B-4B. Pipette wash sub assembly 12 includes discrete tip wash basin 20 with flush array 22, wash tub 58, wash jets 84, vacuum ports 96, and wash basin drain ports 97. Vacuum ports 96 are located within wash tub 58. Vacuum ports 96 are connected to vacuum source 98. Vacuum source 98 may be vacuum pump 24, as shown in FIGS. 1-3. Wash basin drain ports 97 are located within discrete tip wash basin 20 and drain excess wash fluid during a wash cycle. During a wash cycle, vapors may form above pipette wash sub assembly 12 due to the presence of chemicals such as sodium hypochlorite in the wash fluid. Vacuum source 98 creates a vacuum to evacuate the vapors through vacuum ports 96. Vacuum source 98 may be used to evacuate the vapors at any point during or after a wash cycle.

Figure 5A:
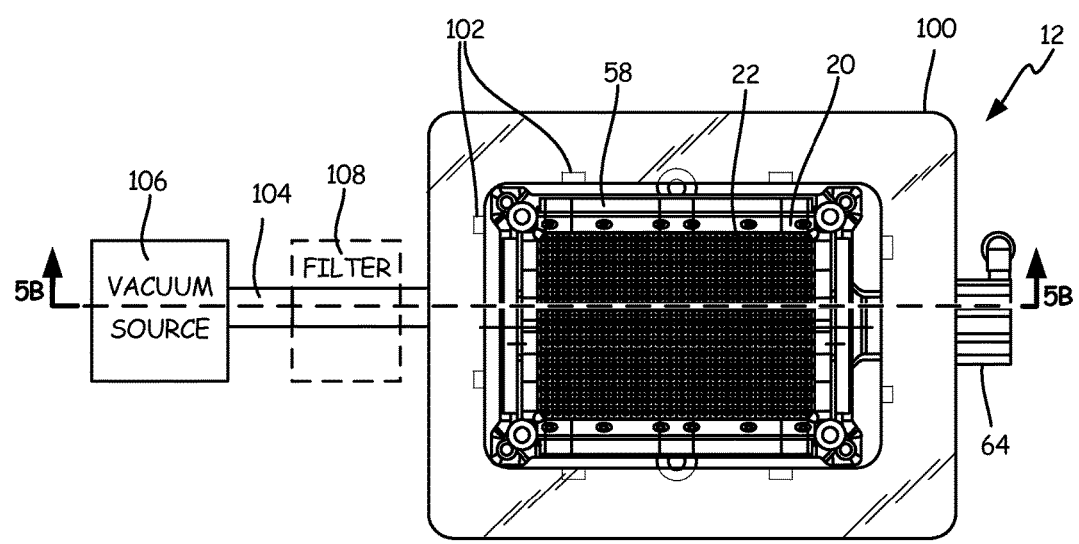
FIG. 5A is a top view of the pipette wash sub assembly of FIG. 3 with a vacuum halo.
Figure 5B:
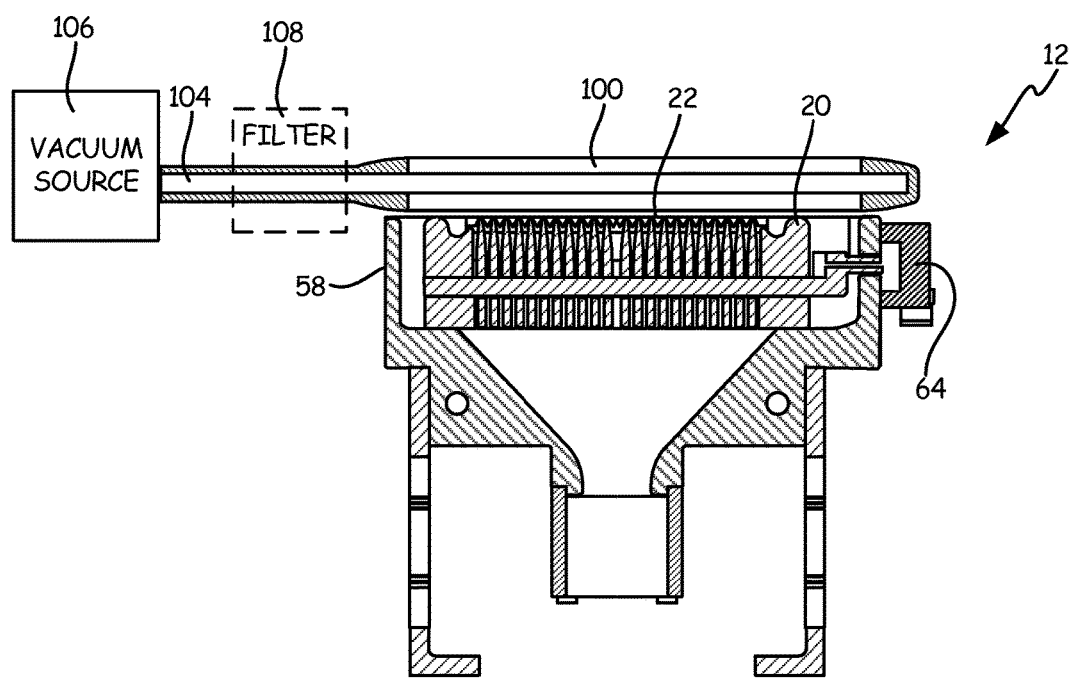
FIG. 5B is a cross-sectional view of the pipette wash subassembly of FIG. 5A along line 5B-5B.

FIG. 5A is a top view of pipette wash sub assembly 12. FIG. 5B is a cross-sectional view of pipette wash subassembly 12 along line 5B-5B. Pipette wash sub assembly 12 includes discrete tip wash basin 20 with flush array 22, wash tub 58, and air cylinder 64, and vacuum halo with vacuum ports 102. Conduit 104 connects vacuum halo 100 to vacuum source 106. Filter 108 may be inserted in conduit 104. Vacuum halo 100 is hollow and is located on top of wash tub 58. During a wash cycle, vapors may form above pipette wash sub assembly 12 due to the presence of chemicals such as sodium hypochlorite in the wash fluid. Vacuum source 106 creates a vacuum to pull the vapors through vacuum ports 102 of vacuum halo 100 into vacuum halo 100 and evacuate the vapors through conduit 104. Filter 108 filters vapors passing through conduit 104. Filter 108 may be a coalescing filter. Vacuum source 106 may be used evacuate the vapors at any point during or after a wash cycle.

Figure 6A:
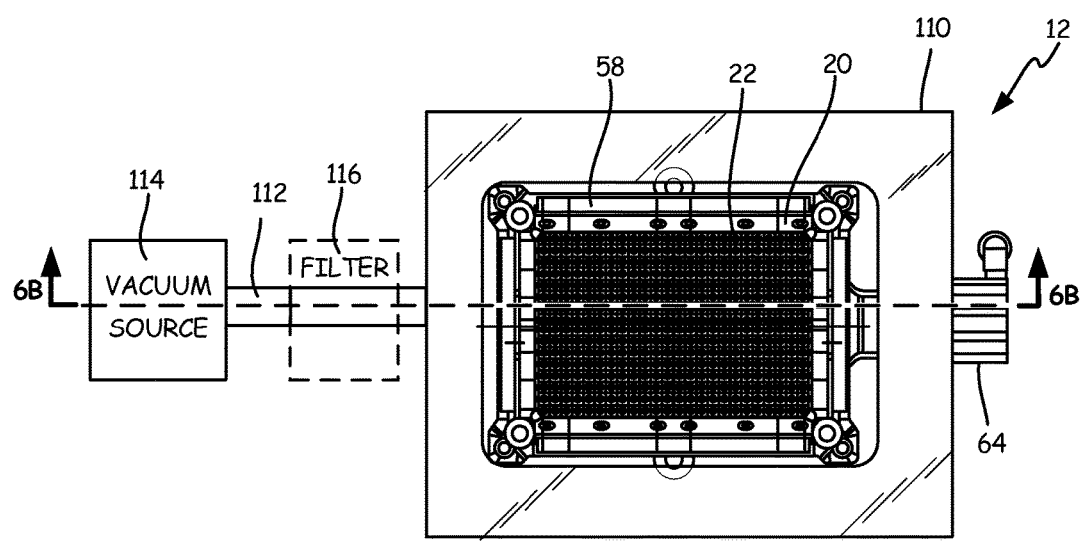
FIG. 6A is a top view of the pipette wash sub assembly of FIG. 3 with a vacuum shroud.
Figure 6B:
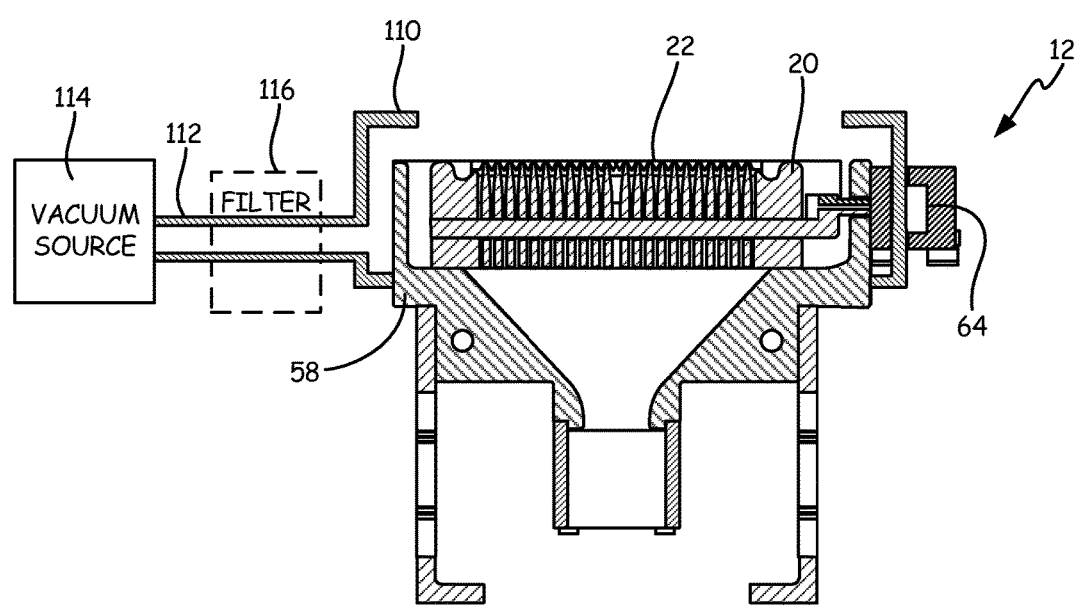
FIG. 6B is a cross-sectional view of the pipette wash subassembly of FIG. 6A along line 6B-6B.

FIG. 6A is a top view of pipette wash sub assembly 12. FIG. 6B is a cross-sectional view of pipette wash subassembly 12 along line 6B-6B. Pipette wash sub assembly 12 includes discrete tip wash basin 20 with flush array 22, wash tub 58, and air cylinder 64, and vacuum shroud 110. Conduit 112 connects vacuum shroud 110 to vacuum source 114. Filter 116 may be inserted in conduit 112. Vacuum shroud 110 is hollow. Vacuum shroud 110 surrounds wash tub 58 and extends above wash tub 58. During a wash cycle, vapors may form above pipette wash sub assembly 12 due to the presence of chemicals such as sodium hypochlorite in the wash fluid. Vacuum source 114 creates a vacuum to pull the vapors into vacuum shroud 110 and evacuate the vapors through conduit 112. Filter 116 filters vapors passing through conduit 112. Filter 116 may be a coalescing filter. Vacuum source 114 may be used to evacuate the vapors at any point during or after a wash cycle.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of washing an array of pipette tips comprising:
    providing a dispensing jet system including the array of pipette tips;
    lowering the array of pipette tips into a wash basin comprising an array of flush ports, the wash basin positioned on a shiftable wash valve plate comprising an array of valves, the shiftable wash valve plate enabled to work with a vacuum source to control vacuum timing;
    generating a vacuum and shifting the wash valve plate such that the residual biological material in the array of pipette tips is evacuated through the array of flush ports and the array of valves; and
    running a wash cycle comprising:
        raising the array of pipette tips from the wash basin;
        filling the wash basin with a primary wash fluid;
        lowering the array of pipette tips into the wash basin;
        running a pipette tip cleansing cycle using dispensing pipette piston cycles of the dispensing jet system to aspirate and dispense the wash fluid in the pipette tips; and
        generating a vacuum such that the primary wash fluid in the array of pipette tips and the wash basin is evacuated through the array of flush ports; and
    positioning a vacuum conduit above the wash basin, the vacuum conduit coupled to a vacuum source to remove vapors from above the wash basin during the wash cycle and/or after the wash cycle.

2. The method of claim 1, wherein the wash cycle is run 1 to 6 times.

3. The method of claim 1, wherein the pipette tip cleansing cycle includes a series of aspirating and dispensing of the primary wash fluid with the array of pipette tips in the primary wash fluid in the wash basin prior to evacuation of the primary wash fluid from the basin.

4. The method of claim 1, wherein the pipette tip cleansing cycle is run 1 to 24 times.

5. The method of claim 1, wherein the primary wash fluid is water.

6. The method of claim 1, wherein the wash basin is filled with 90 mL of the primary wash fluid.

7. The method of claim 1, wherein the wash cycle further comprises filling the wash basin with a secondary wash fluid before filling the wash basin with the primary wash fluid.

8. The method of claim 7, wherein the secondary wash fluid is a solution of 6% sodium hypochlorite.

9. The method of claim 8, wherein the wash basin is filled with 90 mL of a mixture of the primary wash fluid and the secondary wash fluid.

10. The method of claim 1, wherein the wash basin further comprises a plurality of fingers that remove surface area on which the primary wash fluid can sit, allowing effective evacuation of the primary wash fluid through the array of flush ports.

11. The method of claim 1, wherein the array of flush ports comprises 384 ports.

12. The method of claim 1, wherein the array of flush ports comprises 96 ports.

13. The method of claim 1, wherein the conduit includes a filter able to filter vapors passing through conduit from above the wash basin.

14. A system for washing an array of pipette tips comprising:
- a plurality of wash jets;
- a wash basin comprising an array of flush ports for receiving the array of pipette tips, the wash basin positioned on a wash valve plate comprising an array of valves, the wash valve plate being shiftable and configured and arranged to work with a vacuum source to control vacuum timing;
- a primary pump for filling the wash basin with a primary wash fluid;
- a dispensing jet system including the array of pipette tips, the dispensing jet system configured to operate a pipette tip cleansing cycle using dispensing pipette piston cycles of the dispensing jet system to aspirate and dispense the wash fluid in the pipette tips; and
- a vacuum generator for generating a vacuum such that the primary wash fluid and any residual biological material in the array of pipette tips and the wash basin is evacuated through the array of flush ports and the array of valves; and
- a vacuum conduit positioned above the wash basin, the vacuum conduit coupled to a vacuum source and configured and arranged to remove vapors from above the wash basin.

15. The system of claim 14, wherein the primary wash fluid is water.

16. The system of claim 14, wherein the system further comprises a secondary wash fluid for filling the wash basin.

17. The system of claim 16 wherein the secondary wash fluid is a solution of 6% sodium hypochlorite.

18. The system of claim 14, wherein the wash basin further comprises a plurality of fingers that remove surface area on which the primary wash fluid can sit, allowing effective evacuation of the primary wash fluid through the array of flush ports.

19. The system of claim 14, wherein the array of flush ports comprises 384 ports.

20. The system of claim 14, wherein the array of flush ports comprises 96 ports.

21. The system of claim 14, wherein the conduit includes a filter configured and arranged to filter vapors passing through conduit from above the wash basin.

* * * * *